United States Patent [19]
Weiss et al.

[11] Patent Number: 6,027,664
[45] Date of Patent: *Feb. 22, 2000

[54] METHOD AND MAGNETORHEOLOGICAL FLUID FORMULATIONS FOR INCREASING THE OUTPUT OF A MAGNETORHEOLOGICAL FLUID

[75] Inventors: Keith D. Weiss, Eden Prairie, Minn.; J. David Carlson, Cary; Donald A. Nixon, Wilson, both of N.C.

[73] Assignee: Lord Corporation, Cary, N.C.

[*] Notice: This patent is subject to a terminal disclaimer.

[21] Appl. No.: 09/133,148

[22] Filed: Aug. 12, 1998

Related U.S. Application Data

[63] Continuation of application No. 08/544,526, Oct. 18, 1995, Pat. No. 5,900,184.

[51] Int. Cl.[7] .............................. C09K 15/08; C11D 7/50; C11D 7/26; H01F 1/44
[52] U.S. Cl. ................................... 252/62.52; 252/62.55; 252/62.56
[58] Field of Search .............................. 252/62.52, 62.55, 252/62.56

[56] References Cited

U.S. PATENT DOCUMENTS

| | | | |
|---|---|---|---|
| 2,575,360 | 11/1951 | Rabinow | 252/62.52 |
| 2,751,352 | 6/1956 | Bondi | 252/62.52 |
| 2,772,761 | 12/1956 | Janson | 192/21.5 |
| 4,992,190 | 2/1991 | Shtarkman | 252/62.52 |
| 5,167,850 | 12/1992 | Shtarkman | 252/62.52 |
| 5,354,488 | 10/1994 | Shtarkman | 252/62.56 |
| 5,382,373 | 1/1995 | Carlson et al. | 252/62.55 |
| 5,525,249 | 6/1996 | Korndonsky et al. | 252/62.56 |
| 5,578,238 | 11/1996 | Weiss et al. | 252/62.52 |
| 5,599,474 | 2/1997 | Weiss et al. | 252/62.52 |
| 5,645,752 | 7/1997 | Weiss et al. | 252/62.54 |
| 5,667,715 | 9/1997 | Foister | 252/62.52 |
| 5,900,184 | 5/1999 | Weiss et al. | 252/62.52 |

FOREIGN PATENT DOCUMENTS

| | | |
|---|---|---|
| 162371 | 4/1955 | Australia. |
| 4-91196 | 3/1992 | Japan. |

OTHER PUBLICATIONS

Rabinow, Jacob, "The Magnetic Fluid Clutch", AIEE Tran., vol. 67, p. 1308–15, (1948). no month.

German, Randall M., "Particle Packing Characteristics", Metal Powder Industries Federation (1989) p. 6–14 & 135–163. no month.

*Primary Examiner*—C. Melissa Koslow
*Attorney, Agent, or Firm*—Wayne W. Rupert

[57] ABSTRACT

A magnetorheological fluid that includes a carrier component and a magnetizable particle component wherein the magnetizable particle component is a mixture of at least a first particle group having an average particle diameter and a second particle group having an average particle diameter wherein the average particle diameter of said first particle group is 3 to 15 times larger than the average particle diameter of said second particle group.

23 Claims, 3 Drawing Sheets

METHOD AND MAGNETORHEOLOGICAL FLUID FORMULATIONS FOR INCREASING THE OUTPUT OF A MAGNETORHEOLOGICAL FLUID

This is a continuation of commonly-assigned U.S. patent application Ser. No. 08/544,526, filed Oct. 18, 1995, now U.S. Pat No. 5,900,184.

FIELD OF THE INVENTION

The present invention relates to the use of controllable fluids such as magnetorheological fluids in controllable fluid devices. More particularly, this invention relates to a method and controllable fluid formulations for increasing the output of a controllable fluid device.

BACKGROUND OF THE INVENTION

Magnetorheological fluids are magnetic field responsive fluids containing a field polarizable particle component and a liquid carrier component. These rheological fluids (also referred to herein as controllable fluids) are typically used within the working gap of devices such as dampers, shock absorbers, elastomeric mounts, clutches, brakes, and valves to provide varying damping forces, and are activated by the application of a magnetic field.

With regard to the composition of magnetorheological fluids, the particle component of a magnetorheological fluid must comprise a particle or powder that exhibits magnetic field polarizability, and the carrier component can be any oil or liquid medium known in the art, such as silicone oils, silicone copolymers, mineral oils, synthetic hydrocarbons, perfluorinated polyethers, polyesters and the like. Fluid compositions which undergo a change in yield strength of apparent viscosity in the presence of a magnetic field are commonly referred to as Bingham magnetic fluids or magnetorheological materials. Magnetorheological materials normally are comprised of ferromagnetic or paramagnetic particles typically greater than 0.1 microns in diameter, dispersed within a carrier fluid. In the presence of a magnetic field, the particles become polarized and are thereby organized into chains of particles within the fluid. The chains of particles act to increase the apparent viscosity or flow resistance of the overall materials and in the absence of a magnetic field, the particles return to an unorganized or free state and the apparent viscosity or flow resistance of the overall materials is correspondingly reduced.

Desirably, when exposed to a magnetic field the controllable fluids are designed to increase the force output of the device containing the controllable fluid. "Force output" as used herein means the damping force, torque, braking force or similar force depending upon the device. Generally, an increase in the particle amount of the controllable fluid results in an increase in the maximum yield strength of the fluid and, consequently, an increase in the maximum force output of the device. Unfortunately, the real or off-state viscosity of the controllable fluids in the absence of an applied magnetic field increases with increased particle amount. The particle amount, thus, is limited to a level consistent with the real or off-state viscosity requirements for the controllable fluids when the controllable fluids are not subject to a magnetic field.

U.S. Pat. No. 2,575,360 discloses an electromechanically controllable torque-applying device that uses a magnetorheological material to provide a drive connection between two independently rotating components, such as those found in clutches and brakes. A fluid composition satisfactory for this application is stated to consist of 50% by volume of a soft iron dust, commonly referred to as "carbonyl iron powder" (8 microns average size), dispersed in a suitable liquid medium such as a light lubricating oil.

U.S. Pat. No. 4,992,190 and U.S. Pat. No. 5,167,850 disclose rheological materials that are responsive to a magnetic field. The composition of these materials is disclosed to be magnetizable particles and either silica gel or carbon fibers dispersed in a liquid carrier vehicle. The magnetizable particles can be powdered magnetitite or carbonyl iron powders with insulated reduced carbonyl iron powder, such as that manufactured by GAF Corporation, being specifically preferred. The carbonyl iron particles are further described to have a particle size in the range of 3 to 6 microns.

U.S. Pat. No. 2,751,352 and Australian Patent Specification 162,371 disclose magnetorheological fluids wherein the finely divided magnetizable particles are inhibited from precipitating or settling out of the fluid system. The inhibition of particle settling is accomplished by the addition of a minute amount of an oleophobic material to the magnetic fluid. The particle component is further described to be any material possessing magnetic properties and having the dimensions of from 2 to 100 microns, preferably from 5 to 30 microns. Examples of particles include powder iron and iron oxide, with powder iron produced by the decomposition of iron pentacarbonyl being particularly useful.

U.S. Pat. No. 2,772,761 describes an electromagnetic clutch that utilizes a particulate composition that is prepared by mixing iron powder with colloidal graphite dispersed in a resin and then heating the mixture iron powder and colloidal graphite dispersion until the mixture is dry. The dry mixture is used in an electromagnetic clutch. The purpose of the dry mixture is to prevent packing of the iron powder in the electromagnetic clutch. There is no disclosure of a liquid formulation that includes a liquid carrier component.

U.S. Pat. No. 5,354,488 discloses an electrorheological magnetic fluid that consists essentially of a vehicle, magnetizable partilces suspended in the vehicle, and a dispersant. The dispersant is non-magnetizable particles that have no dimension greater than 10 nanometers.

An article entitled "The Magnetic Fluid Clutch" by Jacob Rabinow in AIEE Transactions, Vol. 67, pp. 1308–1315 (1948) mentions that higher magnetic permeabilities can be obtained by using "aggregates of large and small particles." There is no description of any specific aggregates.

A book entitled "Particle Packing Characteristics" by Randall M. German (Metal Powder Industries Federation, Princeton, N.J., ISBN 0-918404-83-5, 1989) describes particle packing phenomenon in general.

None of the patents or publications, however, show methods or formulations of magnetorheological fluids to increase the output of a device containing a magnetorheological fluid without causing an unacceptable increase or degree of variation in the real or off-state viscosity of the magnetorheological fluid.

SUMMARY OF THE INVENTION

Accordingly, it is an object of the present invention to provide magnetorheological fluid formulations which have viscosities comparable to conventional magnetorheological fluids and which increase the force output of a device containing the magnetorheological fluid.

The present invention comprises magnetorheological fluids which exhibit optimum yield strength and force output and minimal variation in viscosity over time and/or conditions. More specifically, the present invention relates to a liquid magnetorheological fluid that includes a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group.

According to the present invention, such fluids are effective to increase the force output of a magnetorheological fluid device in a method that includes positioning a first portion of a magnetorheological fluid in a working gap in the magnetorheological fluid device wherein the first fluid contains a particle component having a fractional packing density equal to at least 0.50; and positioning a second portion of the magnetorheological fluid outside the working gap and in fluid communication with the first portion of the magnetorheological fluid so that when an external field is applied to the first portion of the magnetorheological fluid, the volume percent occupied by the particle component in the first portion of the magnetorheological fluid is increased.

DETAILED DESCRIPTION OF THE INVENTION

As used herein, "particle component" means the portion of the magnetorheological fluid that is comprised of numerous small magnetizable particles. The viscosity of the carrier component alone can range from about 1 centipoise (mPa-sec) to greater than about 250 mPa-sec, with less than about 100 mPa-sec and less than about 50 mPa-sec as the preferred and most preferred viscosity ranges, respectively. Particles in the particle component have an average diameter distribution of from about 0.1 to about 500 microns, with from about 1 to about 500 microns being preferred, about 1 to about 250 microns being particularly preferred, and from about 1 to about 100 microns being especially preferred.

The magnetorheological materials of the present invention comprise a carrier fluid and a particle component which has a fractional packing density of at least 0.50. The carrier component is the continuous phase of the magnetorheological material. In other words, it is a liquid fluid in which the magnetizable particles are suspended. The magnetorheological fluid of the present invention is used in a magnetorheological device without removing the fluid to produce a dry mixture. In fact, the magnetorheological fluid of the present invention would not be useful as a dry mixture because wet fluids provide lubricity and will flow through orifices in devices.

Suitable carrier fluids, for purposes of the present invention, may be found to exist in any of the classes of oils or liquids known to be carrier fluids for magnetorheological materials such as (a) natural fatty oils, (b) mineral oils, (c) polyphenylethers, (d) dibasic acid esters, (e) neopentylpolyol esters, (f) phosphate esters; (g) synthetic cyclopar- affins and synthetic paraffins, (h) unsaturated hydrocarbon oils; (i) monobasic acid esters; (j) glycol esters and ethers; (l) silicate esters; (m) silicone oils; (n) silicone copolymers; (o) synthetic hydrocarbons; (p) perfluorinated polyethers and esters; and (q) halogenated hydrocarbons, as well as mixtures and derivatives thereof. Descriptions of suitable carrier fluids can be found, for example, in U.S. Pat. Nos. 2,751,352 and 5,382,373, both hereby incorporated by reference, and commonly assigned U.S. Pat. Nos. 5,599,474 and 5,578,238, both hereby incorporated by reference. The carrier may also be a fluid such as water, glycols and esters, and mixtures and derivatives thereof. Carrier fluids appropriate to the present invention may be prepared by methods well known in the art and many are commercially available.

The carrier fluid of the present invention is typically utilized in an amount ranging from about 50 to 95, preferably from about 60 to 85, percent by volume of the total magnetorheological fluid. This corresponds to about 11 to 70, preferably about 15 to 41, percent by weight when the carrier fluid and particles of the magnetorheological fluid have a specific gravity of about 0.95 and 7.86 respectively.

The particle component of the magnetorheological fluid of the invention can be any solid which is known to exhibit magnetorheological activity and which has a fractional packing density of at least, preferably greater than, 0.50. Typical particle components useful in the present invention are comprised of, for example, paramagnetic, superparamagnetic or ferromagnetic compounds. Specific examples of particle components useful in the present invention include particles comprised of materials such as iron, iron alloys, iron oxide, iron nitride, iron carbide, carbonyl iron, chromium dioxide, low carbon steel, silicon steel, nickel, cobalt, and mixtures thereof. The iron oxide includes all known pure iron oxides, such as $Fe_2O_3$ and $Fe_3O_4$, as well as those containing small amounts of other elements, such as manganese, zinc, or barium. Specific examples of iron oxide include ferrite and magnetites. In addition, the particle component can comprise any of the known alloys of iron, such as those containing aluminum, silicon, cobalt, nickel, vanadium, molybdenum, chromium, tungsten, manganese, and/or copper. Preferred iron alloys of the invention include iron-cobalt and iron-nickel alloys. The iron-cobalt alloys preferred for use in a magnetorheological fluid have an iron:cobalt ratio ranging from about 30:70 to 95:5, and preferably from about 50:50 to 85:15, while the iron-nickel alloys have an iron:nickel ratio ranging from about 90:10 to 99:1, and preferably from about 94:6 to 97:3. The iron alloys may contain a small amount of other elements, such as vanadium, chromium, etc., in order to improve the ductility and mechanical properties of the alloys. These other elements are typically present in an amount that is less than about 3.0% by weight. Examples of iron-cobalt alloys include HYPERCO (Carpenter Technology), HYPERM (F. Krupp Widiafabrik), SUPERMENDUR (Arnold Eng.) and 2V-PERMENDUR (Western Electric).

The particle component according to the invention is typically in the form of a metal powder having a fractional packing density of at least, preferably greater than, about 0.50. Typical methods for the preparation of metal powders include the reduction of metal oxides, grinding or attrition, electrolytic deposition, metal carbonyl decompositions, rapid solidification, or smelt processing. Various metallic powders that are commercially available include straight iron powders, reduced iron powders, insulated reduced iron powders, cobalt powders, and various alloy powders, such as [48%] Fe/[50%]C/[2%]V.

It has been found that one useful method for producing a particle component that has a fractional packing density of at least or greater than 0.50 is to mix at least two commercially available metal powders that each alone have a fractional packing density of less than 0.50. The resulting mixture, however, has a fractional packing density of at least or greater than 0.50. Preferably, such a mixture includes a first group of particles that has an average particle diameter that is greater than the average particle diameter of a second group of particles. The mixture could also include three, four or more different particle groups that each have a different average particle diameter. The particle groups could also differ in chemical composition or treatments as well as average diamter size. Such mixtures are referred to herein as a "bimodal", "trimodal" or "multimodal" particle distribution depending on the number of different particle groups.

Preferably, the average particle diameter of a first particle group is 3 to 15, preferably 4 to 9, times greater than the average particle diameter of a second particle group. The amount of each particle group relative to the other particle group or groups may vary depending on the difference in average particle diameter or chemical composition.

The particles may be encapsulated or covered by a surface barrier coating in order to prevent the growth of a contaminant layer that may degrade the magnetic properties of the particles. This barrier coating, which preferably encapsulates the entire particle, may be composed of a variety of materials including non-magnetic metals, ceramics, thermoplastic polymeric materials, thermosetting polymers, and combinations thereof. Examples of barrier coating materials are described in commonly assigned U.S. Pat. No. 5,578,238, hereby incorporated by reference.

The preferred particles of the present invention are straight iron powders, reduced iron powders, iron-cobalt alloys, and iron-nickel alloys whether with or without a surface barrier coating.

The particles component typically comprises from about 5 to 50, preferably about 15 to 40, percent by volume of the total magnetorheological materials depending on the desired magnetic activity and viscosity of the overall materials. This corresponds to about 30 to 89, preferably about 59 to 85, percent by weight when the carrier fluid and particles of the magnetorheological fluid have a specific gravity of about 0.95 and 7.86, respectively.

A surfactant to more adequately disperse the particle component in the carrier vehicle may also be optionally utilized in the magnetorheological fluid. Such surfactants include known surfactants or dispersing agents such as ferrous oleate and naphthenate, metallic soaps (e.g., aluminum tristearate and distearate), alkaline soaps (e.g., lithium and sodium stearate), sulfonate, phosphate esters, stearic acid, glycerol monooleate, sorbitan sesquioleate, stearates, laurates, fatty acids, fatty alcohols, and other surface active agents. In addition, the optional surfactant may be comprised of stearic stabilizing molecules, including fluoroaliphatic polymeric esters and titanate, aluminate or zirconate coupling agents. The optional surfactant may be employed in an amount ranging from about 1 to 20 percent by weight relative to the weight of the particle component.

Particle settling may be minimized in the magnetorheological materials of the present invention by forming a thixotropic network as described in commonly assigned U.S. Pat. No. 5,645,752, hereby incorporated by reference. A thixotropic network may be formed in the magnetorheological fluid of the present invention through the utilization of any known thixotropic additive such as hydrogen-bonding thixotropic agents and/or colloidal additives. Examples of such hydrogen-bonding thixotropic agents and colloidal additives are described in previously incorporated U.S. Pat. No. 5,645,752. The thixotropic agents and colloidal additives, if utilized, are typically employed in an amount ranging from about 0.1 to 5.0 and preferably from about 0.5 to 3.0 percent by volume relative to the overall volume of the magnetorheological fluid.

The magnetorheological fluid of the invention may also contain other optional additives such as dyes or pigments, abrasive particles, lubricants, antioxidants, pH shifters, salts, deacidifiers or corrosion inhibitors. These optional additives may be in the form of dispersions, suspensions, or materials that are soluble in the carrier vehicle.

The magnetorheological fluids of the present invention can be prepared by initially mixing the ingredients together by hand (low shear) with a spatula or the like and then subsequently more thoroughly mixing (high shear) with a homogenizer, mechanical mixer or shaker, or dispersing with an appropriate milling device such as a ball mill, sand mill, attritor mill, paint mill, colloid mill or the like, in order to create a more stable suspension.

Evaluation of the mechanical properties and characteristics of the magnetorheological materials or the present invention, as well as other magnetorheological materials, can be obtained through the use of parallel plate and/or concentric cylinder rheometry. The theories which provide the basis for these techniques are further described by S. Oka in *Rheology, Theory and Applications* (volume 3, F. R. Eirich, ed., Academic Press: New York, 1960). The information that can be obtained from a rheometer includes data relating mechanical shear stress as a function of shear strain rate. For magnetorheological materials, the shear stress versus shear strain rate data can be modeled after a Bingham plastic in order to determine the dynamic yield stress and viscosity. Within the confines of this model, the dynamic yield stress for the magnetorheological material corresponds to the zero-rate intercept of a linear regression curve fit to the measured data. The real viscosity of the material is defined as the slope of the line generated by this curve fitting technique. The magnetorheological effect at a particular magnetic field can be further defined as the difference between the dynamic yield stress measured at that magnetic field and the dynamic yield stress measured when no magnetic field is present.

Figure 1:
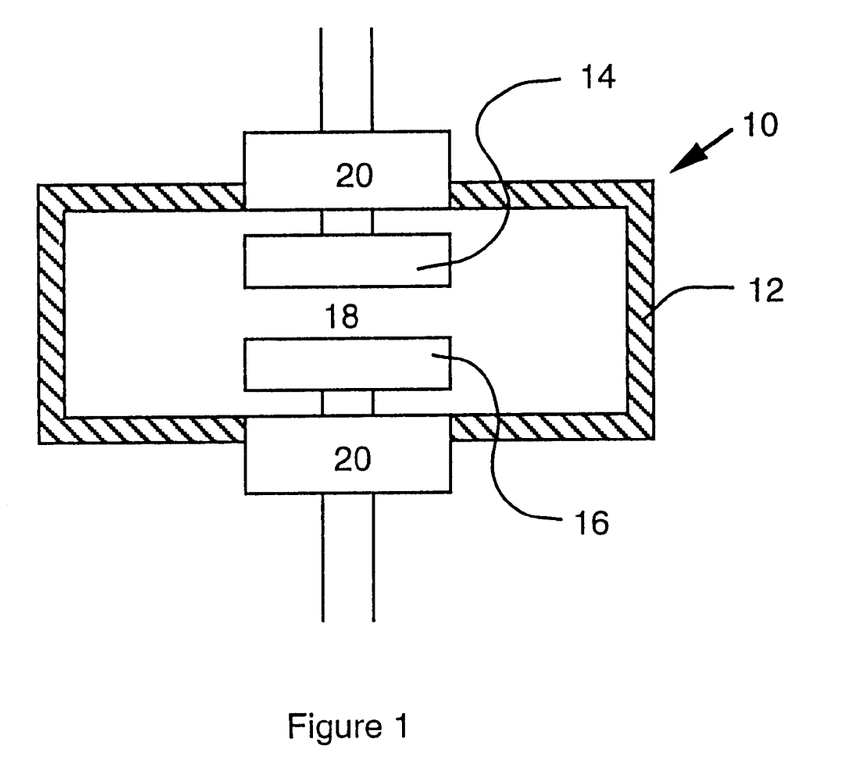
FIG. 1 is a schematic diagram of a test cell.
Figure 2:
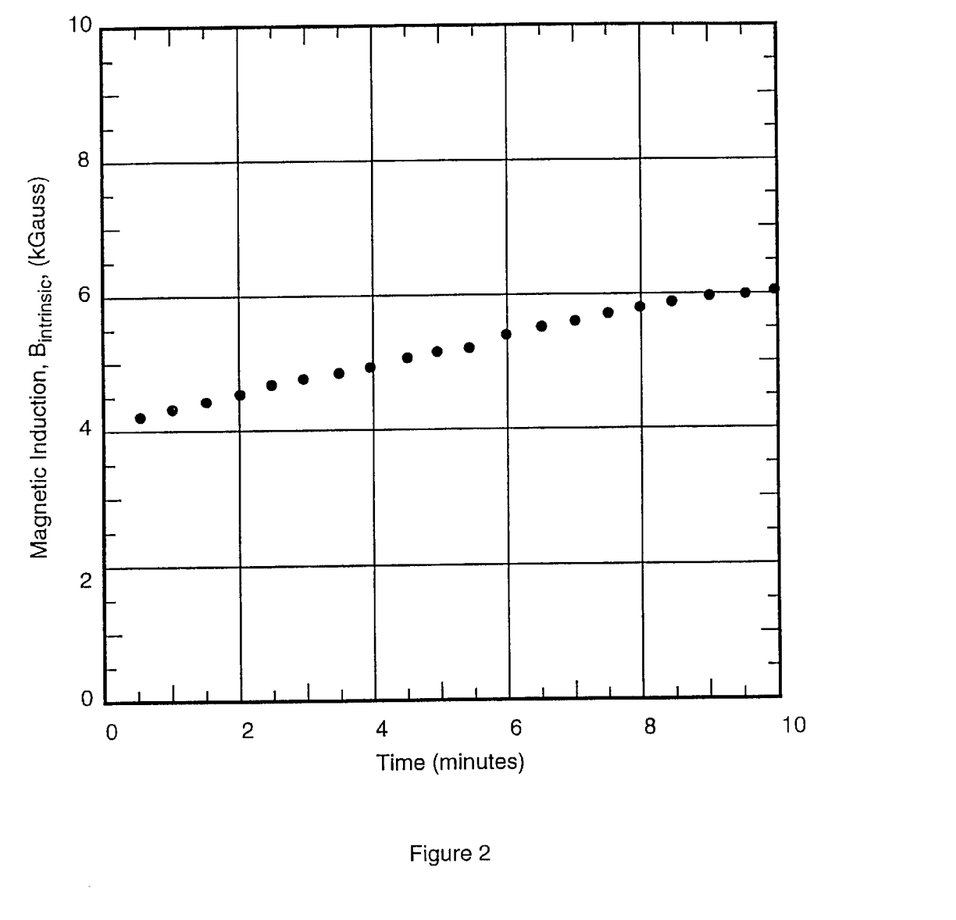
FIG. 2 is a graph of data from Example 3 showing magnetic induction as a function of time.

In a concentric cylinder cell configuration, the magnetorheological material is placed in the annular gap formed between an inner cylinder of radius $R_1$ and an outer cylinder of radius $R_2$, while in a simple parallel plate configuration as shown in FIG. 1, the material is placed in the planar gap formed between an upper plate 14 and a lower plate 12, both with a radius, $R_3$ (not shown). In these techniques, either one of the plates or cylinders is then rotated with an angular velocity co while the other plate or cylinder is held motionless. A magnetic field is typically applied to these cell configurations across the fluid-filled gap, either radially for the concentric cylinder configuration, or axially for the parallel plate configuration. The relationship between the shear stress and the shear strain rate is then derived from this angular velocity and the torque, T, applied to maintain or resist it.

The testing of various application specific devices, such as dampers, mounts, and clutches, that utilize either the magnetorheological materials of the present invention or other magnetorheological materials, is a second method of evaluating the mechanical performance of these materials. The controllable fluid-containing device is simply placed in line with a mechanical actuator and operated with a specified displacement and amplitude and frequency. A magnetic field is appropriately applied to the device and the force output determined from the resulting extension/compression waveforms plotted as a function of time. The methodology utilized to test dampers, mounts, and clutches is well known to those skills in the art of vibration control.

It should be recognized that fractional packing density measures the ability of particles to pack. The fractional packing density measurements of the present invention are conducted using the vibrating technique described below. The general procedure of ASTM B 527-85 was followed with certain modifications described herein. The vibrating technique used to measure fractional packing density of dry powders comprises the steps of adding the dry powder to be measured into a 10 cm³ clear cylinder of known weight and dimensions, placing the cylinder on top of a Model #G-560 Vortex Mixer, manufactured by Scientific Industries, Inc., Bohemia, N.Y. 11716, having a flat rubber disk as the contact surface between the cylinder and mixer, vibrating the cylinder at a setting between 6 and 7 on the mixer for a total of 1.5 minutes, determining the tap density based on the weight of the particles in the cylinder and the resulting height of these particles in the cylinder measured by an analytical balance and a microcalipher, respectively, and dividing the determined tap density by the theoretical density of the powder material to obtain the fractional packing density of the powder. This method eliminates the need to separate the size and shape of particles.

Factors that affect fractional packing density include particle size, particle shape, agitation, surface texture, agglomeration, container size, segregation, bridging, surface active agents, internal powder structure and cohesion. In addition to the above factors, particle size distribution also plays a crucial role in determining particle packing density. For example, a bimodal distribution of spherical iron particles differing in size by seven times provides a large increase in packing density. This increase is caused by the ability of the spherical iron particles with an average size of 4 microns to fit within the interstices formed by spherical iron particles having an average diameter of 28 microns. A similar, but smaller, increase in packing density is also observed in a trimodal distribution of spherical particles. This increase may be demonstrated by the addition of particles having a diameter of 196 microns to the previously described bimodal distributed powder. A paper entitled "Mechanical Packing of Spherical Particles" by R. McGeary, *Journal of the American Ceramic Society* 44(10), 513 provides a thorough description of the particle packing of spherical materials. It should be noted that non-spherical particles are suitable as long as they meet the fractional packing density requirements. Such non-spherical particles may be less expensive and are equally suitable.

In addition to the factors mentioned above, the addition of a liquid carrier component and the application of external fields can also dramatically decrease the interparticle friction and electrostatic force, and thereby greatly enhance the ability of particles to pack. The use of a carrier liquid in quantities greater than 50 percent of the volume of the controllable fluid results in greatly increased particle mobility and packing ability. The presence of a carrier liquid as well as the presence of optional surfactants, dispersants and other additives appears to decrease interparticle friction and electrostatic forces thereby allowing the particles to pack more densely.

A Bingham plastic model, as described by Equation 1 is commonly used to provide a sufficiently accurate description of the rheological behavior exhibited by magnetorheological fluid.

$$\tau_y = \tau_f + \eta \dot{\gamma} \tag{1}$$

Where $\tau_y$=total shear stress (Pa)

$\tau_f$=induced shear stress in Pa at an applied field (f) in units of amps per meter oersteds (for magnetorheological fluids).

$\dot{\gamma}$ =shear rate (S⁻¹)

$\eta$=real viscosity (Pa—S)

The real viscosity, and the field induced dynamic yield stress, $\tau_f$, of magnetorheological fluid are known to be the key fluid properties in basic device design equations.

Within the confines of these device design equations it is known for magnetorheological fluids that the minimum volume of material needed to achieve the desired level of device performance is proportional to the real viscosity of the fluid divided by the square of the dynamic yield stress exhibited by the fluid. In addition, the fluid gap to magnetic pole radius ratio, which is important in the adequate design of a device is found to be proportional to the viscosity of the fluid divided by the dynamic yield stress exhibited by the fluid. In order to design the most effective device, a magnetorheological fluid should exhibit the highest possible yield stress and the lowest possible viscosity.

Selection of the diameter size distribution of the particles is more important for magnetorheological fluids than for the dry magnetic powders used in magnetic powder clutches. Magnetic powder clutches, which are generally dry or contain a very small volume fraction of liquid, cannot provide the necessary particle mobility to allow the particles to achieve a particle packing in the working gap of a device. In addition, magnetic powder clutches generally contain only enough particles to occupy the working gap. As a result, even if the particles were mobile there would be no extra particles available to move into the working gap. In contrast, magnetorheological fluid dampers, valves, clutches, brakes, vibration mounts and other similar devices are contructed to contain an excess of the amount of magnetorheological fluid required to occupy the working gap via a reservoir of magnetorheological fluid outside of the working gap from which particles can migrate into the working gap.

In FIG. 1, a test cell 10, including a fluid containment compartment 12, encloses a first circular plate 14 and a second circular plate 16 with plates 14 and 16 being generally parallel. A magnetorheological fluid fills a working gap 18 between plates 14 and 16 and at least a portion of the fluid containment compartment 12. An external field is applied generally axially to plates 14 and 16 by a field generator 20. Plates 14 and 16 are then rotated to determine the relationship between the shear stress and the shear strain rate.

As used herein, "working gap" means a portion of a device through which magnetorheological fluid flows (valve or damper) or in which the magnetorheological fluid is directly sheared (brake or clutch) and where the magnetorheological fluid can be subjected to an applied magnetic field. In other words, it is the gap or void between magnetic poles that is filled with magnetorheological fluid.

In the practice of the method of the present invention, a first portion of a magnetorheological fluid is positioned in working gap 18 in a magnetorheological fluid device, such as the device shown schematically in FIG. 1. The magnetorheological fluid comprises a particle component and a carrier component with the particle component having a fractional packing density equal to at least 0.50. A second portion of the magnetorheological fluid is positioned outside the working gap, but in fluid communication with the magnetorheolgical fluid in the working gap, i.e., in fluid containment compartment 12. Upon polarization of the particles in the magnetorheological fluid by application of an external field, particles from the second portion move into the working gap thus increasing the force output of the magnetorheological fluid device as a result of the increased particle concentration in the magnetorheological fluid in the working gap. In other words, during application of an external field, the particle volume concentration in the first portion of the magnetorheological fluid is greater than the static or off-state overall particle volume concentration. By "static or off-state overall particle volume concentration" it is meant the average particle volume concentration exhibited by the combination of the magnetorheological fluid in the first portion and the controllable fluid in the second portion when a magnetic field is not being applied.

The volume concentration of particles in the working gap can be increased to values greater than are acceptable in the magnetorheological fluid that occupies the fluid containment compartment of the device as a whole. The apparent viscosity limitations imposed on the magnetorheological fluid as a whole are not necessary in the magnetorheological fluid in the working gap during application of the external field. The volume concentration of particles in the working gap can thus be increased beyond the concentration limits imposed by apparent viscosity limitations to provide an increased force output while still using a magnetorheological fluid which has an overall particle volume concentration within the concentration range imposed by apparent viscosity limitations when particles having a suitable fractional packing density are used in the magnetorheological fluid. For example, commercial application of a device might require that the magnetorheological fluid have an overall particle concentration of significantly less than 50% of the total volume of the magnetorheological fluid. This invention allows the localized particle concentration of the magnetorheological fluid portion located in the working gap to adjust to volume concentrations greater than 50% upon application of a magnetic field.

The fluids of the present invention not only increase the output of the magnetorheological fluid devices in which they are used, but they also result in a decreased fluid cost, a decreased fluid weight, and an increased ability to stabilize the fluid particles from sedimentation. These advantages arise at least in part from the ability to reduce the volume fraction of the particles present in the magnetorheological fluid. According to the present invention, a fluid containing a particle component with efficient packing will exhibit a higher yield strength in a device such as described in FIG. 1 than a prior art fluid. Thus, the volume fraction of the particles can be decreased while still exhibiting the required strength. The decrease in particle volume equates to a reduction in fluid cost since the particles are more expensive than the carrier fluid, and in an increase in stability because of the lower particle content and the greater carrier fluid volume available for the addition of stabilizers. The fluids of the present invention, while they provide greater yield strengths, do not exhibit a significant increase in viscosity over prior art fluids, and may in some instances be less viscous because of the lower particle concentrative requirements to meet a given yield strength requirement.

Examples of the invention are described below. In each example, the percentages given for each particle group of the particle mixtures are in terms of weight percent based on the total weight of the particle component.

EXAMPLE 1

The fractional packing densities for a variety of iron particle components were determined using the vibrating technique described above. Magnetorheological fluids were then prepared using the respective iron particle components. The magnetorheological fluids were prepared so that the iron particle volume fraction was held constant at 0.20. A total of 2% based on the weight of the particle component of a dispersant (PEG-200 Dioleate available from PPG Industries) was added, and 2.8% based on the fluid volume of a thixotropic additive such as a surface treated fumed silica (Cabosil® TS-720, manufactured by Cabot Corporation) was added. The carrier fluid was a hydrocarbon based oil (Drakeol® 10B manufactured by Penreco Inc.) which constituted the remainder of the magnetorheological fluid. An example of the above formulation would be 20 vol % of iron (78.60 grams), 2 wt % of dispersant, based on particle weight (1.65 grams), 2.8 vol % of a thixotropic additive (3.22 grams), with the remainder being carrier fluid (32.14 grams). The carrier fluid containing the listed ingredients was initially prepared using minimal agitation by hand or a paint shaker. The mixture was then subjected to high shear conditions for several minutes using a high speed disperser having a 16 tooth disperser head. The dynamic yield stress of each of the resulting formulations was determined using conventional couette cell used above contained two working gaps across which a magnetic field was placed. Excess fluid was also present between these two working gaps, below the lower gap and above the upper gap. The test results are shown below in Table 1.

TABLE 1

| Description of Iron Particle Component | Fractional Packing Density | Dynamic Yield Stress (kPa) |
| --- | --- | --- |
| a) El Core powder 908 (SCM Metal Products, Inc.) | 0.38 | 95 |
| b) Atomet 95G (Quebec Metal Powders Limited) | 0.39 | 94 |
| c) −200 mesh (#00737, Johnson Matthey Company) | 0.40 | 96 |
| d) Ancor Steel (Hoeganease, an Interlake Company) | 0.43 | 104 |
| e) Carbonyl Iron, Grade-S-1640 (ISP Technologies, Inc.) | 0.47 | 156 |
| f) Mixture of 50% Grade-S-1640 & 50% 200 mesh | 0.52 | 176 |
| g) Mixture of 50% Grade-S-1640 & 50% Atomet 95G | 0.55 | 187 |
| h) Mixture of 50% Grade-S-1640 & 50% Ancor Steel | 0.61 | 193 |

The test results demonstrate the general trend that the dynamic yield stress of a magnetorheological fluid increases with increasing fractional packing density. The test results also demonstrate that several commercially available iron powders (a-e) are outside the specifications of the present invention. A mixture of these powders (f-h) is necessary to obtain optimum yield strength values as specified by the present invention.

EXAMPLE 2

The fractional packing densities for a variety of ferromagnetic powders were determined using the vibrating technique described above. The results of the measurements are listed in Table 2 below.

TABLE 2

| Description of Ferromagnetic Particle Component | Fractional Packing Density |
|---|---|
| a) Carbonyl iron, Micropowder ™ Grade-S-3700 (ISP Technologies, Inc.) | 0.38 |
| b) Carbonyl iron, Micropowder ™ Grade-S-1000 (ISP Technologies, Inc.) | 0.30 |
| c) Carbonyl iron, Micropowder ™ Grade-R-2521 (ISP Technologies, Inc.) | 0.31 |
| d) Carbonyl iron, Micropowder ™ Grade-N-1370 (ISP Technologies, Inc.) | 0.42 |
| e) Carbonyl iron, Micropowder ™ CIP-S-5641 (ISP Technologies, Inc.) | 0.46 |
| f) Fe50/Ni50 alloy powder, FE076010 (Goodfellow Corporation) | 0.48 |
| g) El Core iron powder A-233 (SCM Metal Products, Inc.) | 0.42 |
| h) 200 mesh iron (U.S. Metals, Inc.) | 0.45 |
| i) Fe58/Ni42 alloy powder, FE136010 (Goodfellow Corporation) | 0.37 |
| j) Iron oxide (#3460, Ceramic, Color & Chemical Manufacturing) | 0.11 |
| k) Ferrite, iron oxide (#73302-0, Steward Manufacturing Co.) | 0.42 |
| l) Stainless steel powder, FE246020 (Goodfellow Corporation) | 0.49 |
| m) Mixture of 55% 200 mesh iron, 30% Atomet 95G, 15% Grade-S-1640 | 0.52 |
| n) Mixture of 33% 200 mesh iron, 33% Atomet 95G, 34% Grade-S-1640 | 0.59 |

The data of Table 2 demonstrate that commercially available magnetizable powders (a-l) typically do not exhibit the fractional packing density needed to optimize the yield strength of the magnetorheological fluid and that improvement in the fractional packing density can be achieved by mixing several different types of commercially available powders (m-n).

EXAMPLE 3

The fractional packing density for an iron powder was determined five times using the vibrating technique described above to check reproducibility of the measurements. The test results are listed in Table 3 below and demonstrate that this vibrating measurement technique provides very constant and reliable results.

TABLE 3

| Description of Iron Particle Component | Fractional Packing Density |
|---|---|
| Carbonyl iron, Micropowder ™ Grade-S-1640 (ISP Technologies, Inc.) | 0.47 |
| Carbonyl iron, Micropowder ™ Grade-S-1640 (ISP Technologies, Inc.) | 0.47 |
| Carbonyl iron, Micropowder ™ Grade-S-1640 (ISP Technologies, Inc.) | 0.47 |
| Carbonyl iron, Micropowder ™ Grade-S-1640 (ISP Technologies, Inc.) | 0.46 |
| Carbonyl iron, Micropowder ™ Grade-S-1640 (ISP Technologies, Inc.) | 0.46 |

EXAMPLE 4

The fractional packing density of various mixtures of two different forms of iron particles were determined using the vibrating technique described above. The magnetorheological fluids were then prepared using respective iron particle mixtures occupying 25% of the total volume (982.5 grams), 0.5% (1.92 grams) Xanthan gum based on the weight of the carrier component (Kelzan® AR, Kelco- A division of Merck & Co.), 5.0% (19.17 grams) sodium nitrate based on the weight of the carrier component (Aldrich Chemical Company), with the remainder being a carrier fluid mixture of 50:50 ethylene glycol (191.68 grams). The fluids were initially prepared by mixing the listed ingredients together and providing minimal agitation by shaking the container by hand or on a paint shaker. The mixtures were then subjected to high shear conditions for several minutes using a high speed disperser having a 16 tooth disperser head. The resulting formulations were then placed in a flow valve through which 3 amps of electrical current was applied to generate a magnetic field of about 3000 oersted. Excess fluid was available at both the inlet and outlet of the valve opening. The above formulations were pumped through the valve with the change in pressure being recorded as the magnetic field was increased. During the measurement of the final two formulations, stiction or particle jamming was observed, which prohibited accurate measurement of the dynamic yield stress for these two formulations.

TABLE 4

| Description of Iron Particle Mixture | Fractional Packing Density | Dynamic Yield Stress (kPa) | Plastic Viscosity (mPa-sec) |
|---|---|---|---|
| a) 100% Grade-S-1640 and 0% Atomet 95G | 0.47 | 90 | 89 |
| b) 80% Grade-S-1640 and 20% Atomet 95G | 0.49 | 97 | 81 |
| c) 60% Grade-S-1640 and 40% Atomet 95G | 0.52 | 109 | 87 |
| d) 50% Grade-S-1640 and 50% Atomet 95G | 0.53 | 113 | 95 |
| e) 40% Grade-S-1640 and 60% Atomet 95G | 0.53 | 123 | 113 |
| f) 20% Grade-S-1640 and 80% Atomet 95G | 0.48 | stiction | 176 |
| g) 0% Grade-S-1640 and 100% Atomet 95G | 0.39 | stiction | 306 |

This example demonstrates that the commercial powders (a & g) do not meet the requirements of the present invention for fluid optimization. In fact, magnetorheological fluids prepared with these commercial powders or mixtures of powders that are outside the scope of the present invention (a, b, f, & g) either show smaller dynamic yield strength values, particle stiction, or a dramatic increase in viscosity as compared to magnetorheological fluids containing particle mixtures that fall within the scope of the invention (c-e). Mixtures appropriate to the present invention exhibit improved yield strength with minimal change in viscosity. If the amount of the particle group having the larger particle size is too great, the fractional packing density will be too low. If the amount of the particle group having the smaller particle size is too low, the plastic viscosity will be too high. In general, the weight percent of each particle group of a particle mixture should be roughly equal. For example, each particle group of a bimodal particle distribution should comprise about 40 to 60 weight percent based on the total weight of the particle component. In general, each particle group of a trimodal particle distribution should comprise 20 to 40 weight percent based on the total weight of the particle component.

EXAMPLE 5

Figure 3:
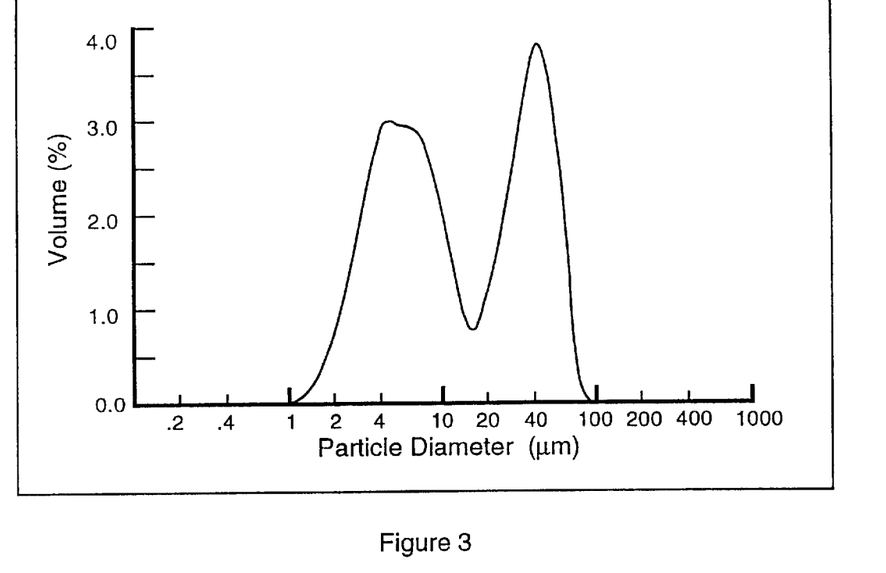
FIG. 3 is a graph of particle size as a function of volume for the carbonyl iron particles discussed in Example 5.
Figure 4:
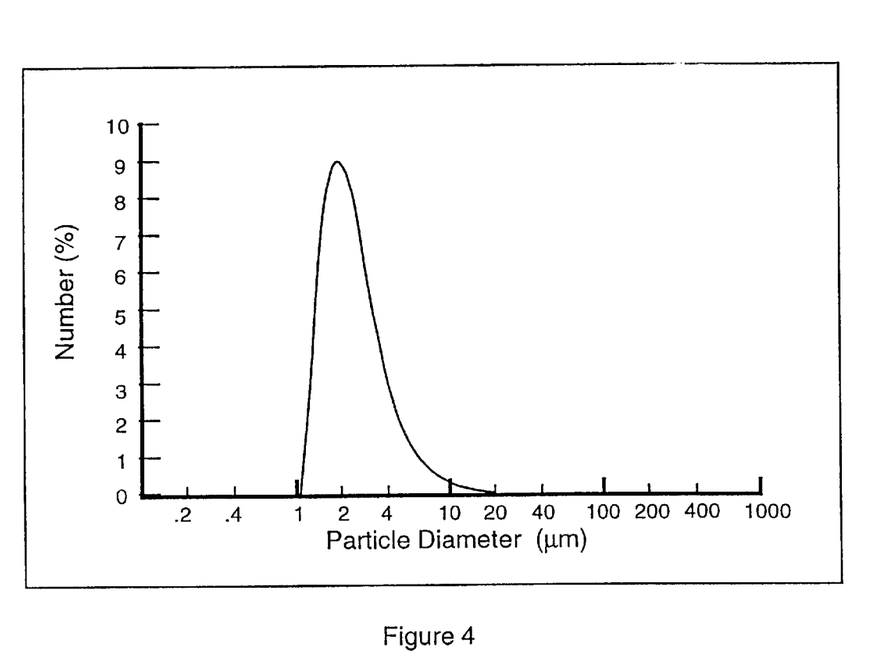
FIG. 4 is a graph of particle size as a function of particle count for the carbonyl iron particles discussed in Example 5.

The preferred 50:50 mixture of Grade-S-1640: Atomet 95G (Example 4, formulation d) exhibits a bimodal particle distribution in particle size as shown in FIGS. 3 and 4. It has been found that the smaller carbonyl iron particles (Grade S-1640) exhibit a particle size of about 5 microns with the larger iron powder (Atomet 95 G) exhibiting a particle size at 35 microns, 7 times larger. However, it has also been found that there are a considerably larger number of smaller particles than the larger iron powder particles in the formulation. This is observed in FIG. 4 by looking at the number % particle size which shows that particles with an average size of 2.89 microns are most abundant in the formulation. The presence of a large number of small particles is needed to efficiently pack within the interstices made by the larger particles. This example demonstrates that the preferred particles of the present invention typically exhibit a bimodal distribution in particle size.

EXAMPLE 6

Several magnetorheological fluids were prepared by high speed dispersion using 20 volume % iron particles, 1 weight % polyoxyethylene (2) stearyl ether (Brij® 72, ICI Specialties) based on the weight of the particles, with the remainder being silicone oil (1000 mPa-sec, Union Carbide Specialty Chemicals Co.). Several additional magnetorheological fluids were prepared according to the formula above using 10 mPa-sec silicone oil (Union Carbide Specialty Chemicals Co.). These low viscosity formulations also contained 3.0 volume % of a thixotropic additive (Cabosil TS-720). The thixotropic additive replaced an equivalent volume of carrier oil in the formulation. The resulting formulations were then placed in a double couette cell (knife blade cell) to measure the dynamic yield strength of the respective magnetorheological fluids. Similar to other controlled devices above, this cell also allows excess fluid to be present below and above the gap, so as to maximize volume fraction of particles within the gap. The yield stress values measured for the above formulations and a further description of the type of iron particles and silicone oil are provided in Table 5 below.

TABLE 5

| Description of Iron Particle Component | Dynamic Yield Strength (kPa) when silicone oil has a viscosity of 1000 mPa-sec | Dynamic Yield Strength (kPa) when silicone oil has a viscosity of 10 mPa-sec |
| --- | --- | --- |
| Grade S-1640 | 35 | 45 |
| mixture of 50% Grade-S-1640 and 50% Atomet | 30 | 73 |
| Atomet 95G | 20 | 31 |

The data of Table 5 demonstrate that a high viscosity carrier oil slows down the migration of particles into the working gap, hence hinders the efficient packing of the particles in the gap and diminishes any observed increase in dynamic yield strength. The preferred carrier components in the present invention are low in viscosity.

What is claimed is:

1. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group and wherein the particles of each of said first particle group and said second particle group have an average particle diameter of at least about 1 micron.

2. The magnetorheological fluid of claim 1 wherein said carrier component has a viscosity between about 1 and about 250 centipoise.

3. The magnetorheological fluid of claim 2 wherein said carrier component has a viscosity of less than about 50 centipoise.

4. The magnetorheological fluid of claim 1 wherein said carrier component is present in an amount of about 50 to about 95 volume percent of said magnetorheological fluid and said particle component is present in an amount of about 5 to about 50 volume percent of said magnetorheological fluid.

5. The magnetorheological fluid of claim 1 wherein said carrier component further comprises a dispersant.

6. The magnetorheological fluid of claim 1 wherein said particle component is selected from the group consisting of iron, iron alloy, iron oxide, iron nitride, iron carbide, carbonyl iron, chromium dioxide, low carbon steel, silicon steel, nickel, cobalt, and a mixture thereof.

7. The magnetorheological fluid of claim 1 wherein said mixture comprises 40 to 60 weight percent of said first particle group and 60 to 40 weight percent of said second particle group, based on the total weight of the particle component.

8. The magnetorheological fluid of claim 5 wherein the dispersant is selected from an oleate, naphthenate, sulfonate, phosphate ester, stearic acid, stearate, glycerol monooleate, sorbitan sesquioleate, laurate, fatty acid and fatty alcohol.

9. The magnetorheological fluid of claim 8 wherein the dispersant comprises a stearate.

10. The magnetorheological fluid of claim 1 wherein the average particle diameter of said first particle group is 4 to 9 times larger than the average particle diameter of said second particle group.

11. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group and wherein the particles of said second particle group are generally spherical.

12. The magnetorheological fluid of claim 11 wherein said particle component comprises finely divided solids having an average diameter from about 0.1 micron to 500 microns.

13. The magnetorheological fluid of claim 11 wherein the magnetizable particles have an average diameter of at least about 1 micron.

14. The magnetorheological fluid of claim 11 wherein said carrier component is present in an amount of about 50 to about 95 volume percent of said magnetorheological fluid and said particle component is present in an amount of about 5 to about 50 volume percent of said magnetorheological fluid.

15. The magnetorheological fluid of claim 11 wherein said carrier component further comprises a stearate.

16. The magnetorheological fluid of claim 11 wherein the particles of the first particle group comprise iron powder and the particles of the second particle group comprise carbonyl iron.

17. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group and wherein said carrier component is selected from the group consisting of natural fatty oil, mineral oil, polyphenylether, dibasic acid ester, neopentylpolyol ester, phosphite ester, synthetic cycloparaffin, synthetic paraffin, unsaturated hydrocarbon oil, monobasic acid ester, glycol ester and ether, fluorinated ester and ether, silicate ester, silicone oil, silicone copolymer, synthetic hydrocarbon, perfluorinated polyether and ester, halogenated hydrocarbon and water and mixtures and derivatives thereof.

18. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group and wherein said particle component is selected from the group consisting of iron, iron oxide, iron alloy and a mixture thereof.

19. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 4 to 9 times larger than the average particle diameter of said second particle group.

20. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group and wherein the particles of said second particle group comprise carbonyl iron.

21. The magnetorheological fluid of claim 18 wherein the particles of the first particle group comprise iron powder.

22. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group and wherein the particles of said first particle group comprise iron powder.

23. A magnetorheological fluid comprising a magnetizable particle component and a carrier component wherein said magnetizable particle component is a mixture of at least a first particle group having an average particle diameter and a second particle group having an average particle diameter wherein the average particle diameter of said first particle group is 3 to 15 times larger than the average particle diameter of said second particle group, further comprising a third particle group having an average particle diameter wherein the average particle diameter of said third particle group is different than the average particle diameter of said first and second particle groups.

* * * * *